United States Patent
Hackstein et al.

(10) Patent No.: US 10,436,621 B2
(45) Date of Patent: Oct. 8, 2019

(54) DETECTION FOR LOCALIZING A PARTICLE

(71) Applicant: SIEMENS AKTIENGESELLSCHAFT, München (DE)

(72) Inventors: Holger Hackstein, Dietzenbach (DE); Christian Morhart, Obertraubling / Niedertraubling (DE); Florian Poprawa, München (DE); Andreas Ziroff, München (DE); Dominik Zoeke, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 579 days.

(21) Appl. No.: 15/039,435

(22) PCT Filed: Nov. 27, 2014

(86) PCT No.: PCT/EP2014/075795
§ 371 (c)(1),
(2) Date: May 26, 2016

(87) PCT Pub. No.: WO2015/078960
PCT Pub. Date: Jun. 4, 2015

(65) Prior Publication Data
US 2016/0377466 A1     Dec. 29, 2016

(30) Foreign Application Priority Data
Nov. 29, 2013   (DE) .................. 10 2013 224 507

(51) Int. Cl.
*G01F 1/66*     (2006.01)
*G01N 15/06*    (2006.01)
(Continued)

(52) U.S. Cl.
CPC .......... *G01F 1/66* (2013.01); *G01N 15/0656* (2013.01); *G01N 15/1031* (2013.01);
(Continued)

(58) Field of Classification Search
CPC .............................. G01F 1/66; G01N 15/0656
See application file for complete search history.

(56) References Cited

U.S. PATENT DOCUMENTS 5,133,602 A * 7/1992 Batchelder ......... G01N 15/0205
356/364
5,805,107 A    9/1998 Schroth et al.
(Continued)

FOREIGN PATENT DOCUMENTS

CN    101573594 A    11/2009
EP    0802427 A2     10/1997
(Continued)

OTHER PUBLICATIONS

Chinese Office Action for Chinese Application No. 201480064994.1, dated May 30, 2018.
(Continued)

*Primary Examiner* — Mohamed Charioui
(74) *Attorney, Agent, or Firm* — Lempia Summerfield Katz LLC

(57) ABSTRACT

Detection for localizing at least one particle moving in a flow includes emitting a transmission signal by a transmitter, and receiving a reflected reception signal. The reflected reception signal is frequency and phase modulated in comparison with the transmission signal. The reflected reception signal is convolved with at least one kernel representative of a conjugate estimated channel pulse response. A reconstructed particle position function is formed, and the position of the particle is determined from the reconstructed particle position function.

20 Claims, 2 Drawing Sheets

(51) Int. Cl.
  *G01N 15/10*    (2006.01)
  *G01S 13/58*    (2006.01)
  *G01S 13/90*    (2006.01)
  *G01N 15/00*    (2006.01)
  *G01S 13/46*    (2006.01)

(52) U.S. Cl.
  CPC .... *G01S 13/583* (2013.01); *G01N 2015/0026* (2013.01); *G01N 2015/0046* (2013.01); *G01N 2015/0053* (2013.01); *G01S 13/9064* (2019.05); *G01S 2013/466* (2013.01)

(56) References Cited

U.S. PATENT DOCUMENTS

| | | | |
|---|---|---|---|
| 8,044,846 | B1 | 10/2011 | Urkowitz et al. |
| 2008/0156107 | A1 | 7/2008 | Ao et al. |
| 2011/0009745 | A1* | 1/2011 | Seifer .................. G01F 1/74 600/437 |

FOREIGN PATENT DOCUMENTS

| | | |
|---|---|---|
| EP | 2618179 A1 | 7/2013 |
| WO | WO2011076346 A1 | 6/2011 |
| WO | WO2012051216 A1 | 4/2012 |

OTHER PUBLICATIONS

German office Action for related German Application No. 10 2013 224 507.6 dated Aug. 5, 2014, with English Translation.

O. Bonnefous et al.: "Time Domain Formulation of Pulse-Doppler Ultrasound and Blood Velocity Estimation by Cross Correlation", Ultrasonic Imaging 8, pp. 73-85, Academic Press, Inc., 0161-7346/86 $3.00, 1986.

PCT International Search Report and Written Opinion of the International Searching Authority dated Feb. 19, 2015 for corresponding PCT/EP2014/075795.

* cited by examiner

DETECTION FOR LOCALIZING A PARTICLE

CROSS-REFERENCE TO RELATED APPLICATIONS

This application is the National Stage of International Application No. PCT/EP2014/075795, filed on Nov. 27, 2014, which claims priority to DE102013224507.6, filed Nov. 29, 2013, both of which are hereby incorporated by reference in its entirety.

FIELD

The disclosure relates to a detection method and device for localizing at least one particle moving in a flow.

The detection and localization of particles in a flow, and of particle clusters with an increased concentration in flows, plays an important role in many situations. An exemplary problem scenario is the monitoring and control of combustion processes. Here, for an ideal combustion process, a mass concentration of the fed substance that is homogeneous in time in the airflow is required. However, mechanical and flow-dynamic effects lead to the formation of inhomogeneities, so-called particle strands, and therefore to an inhomogeneous distribution of the mass flow. In order to introduce countermeasures, such inhomogeneities are identified and, the position thereof is determined.

Systems based on ultrasonic or microwave sensors are conventionally used for measuring a volume or mass flow without directly introducing a measurement apparatus into the airflow. Information about volume and mass distribution is obtained from the ratio of absorbed to reflected signal power. In the case of a plurality of coherent sensors, information about volume and mass distribution is obtained from transmitted power, and from a time-of-flight measurement. Here, microwave systems, for example, are based on a power measurement. Here, measurement errors occur more frequently when inhomogeneous substance concentrations occur, e.g. due to strand formation.

SUMMARY AND DESCRIPTION

It is the object of the disclosed embodiments for localizing a particle to improve the spatial resolution capability of a system for particle measurement, in particular of a microwave system.

The scope of the disclosed embodiments is defined solely by the appended claims and is not affected to any degree by the statements within this summary. The present embodiments may obviate one or more of the drawbacks or limitations in the related art.

One embodiment of a detection method for localizing at least one particle moving in a flow includes the acts of emitting a transmission signal by a transmitter and receiving a reflected reception signal. The reflected reception signal is frequency-modulated and phase-modulated in comparison with the transmission signal, by a receiver. In order to improve the spatial resolution capability, provision is made here for subsequently convolving the reception signal with at least one kernel that represents a conjugate, estimated channel pulse response. The reception signal may be convolved with an (integration) kernel to form a reconstructed particle position function, and the position of the particle is determined from the reconstructed particle position function. Thus, conversely, a convolution of the kernel or integration kernel with an ideal particle position function describes the reception signal. Below, the terms kernel and integration kernel are used synonymously. In particular, the transmission and reception signals can be microwave signals. A substantial advantage of the method described here lies in the employed deterministic signal model, enabling a high adaptability to different situations. Advantageously, individual positions in the flow may be "illuminated" in a targeted manner (e.g. the kernel fitting to a specific position can be used in a targeted manner for the convolution). Thus, specific spatial regions may be analyzed in a targeted and precise manner and, correspondingly, it is possible to detect particles that are localized there. A further advantage is that the processing leads directly to a specific image of the spatial coordinates such that a manual, visual interpretation is also possible. If a plurality of sensors are used for multidimensional localization or simply for increasing the detection reliability or detection accuracy, there is no need for a phase or frequency precise coherence of the sensors. Hence there is no need for adjustment of the sensors amongst themselves since the method only evaluates the data from a single sensor in each case. Extending the method by additional sensors or by the data of additional sensors can thus be readily carried out. Moreover, the method does not assume a specific transmission signal form or sensor architecture. A mono-frequency single-channel sensor is realizable with a low switching complexity and therefore in a cost-effective manner, is sufficient. By contrast, the method can likewise be applied in the case of more complicated architectures, for example in a sensor with a frequency-modulated continuous-wave (FMCW) signal form. Then, due to additional possibilities of signal processing, a correspondingly higher capability (e.g., a lower error rate and false detection rate and a higher localization accuracy) is to be expected. It is also advantageous that the required convolution operations can be represented compactly in the frequency domain and can be carried out efficiently with logarithmic complexity.

In a preferred embodiment, provision is made for the convolution to be carried out a number of times with a different kernel of a family of kernels in each case. A kernel of the family in each case corresponds to a different expected particle position function. The position is determined from the obtained family of reconstructed particle position functions. Individual positions in the flow are analyzed, as well as a plurality of positions are analyzed. Certain positions are also masked (e.g., cannot be analyzed) in a targeted manner. The number and form of the kernel functions is moreover variable, and the kernels are present per se in a separated form. Accordingly, the method can also be scaled and parallelized, depending on desired resolution capability and available computational power.

Here, provision is made in a further embodiment for the kernels to be assigned in each case to particle position functions that, in each case, describe particle positions that are distributed along a principal movement direction of the particles in the flow (e.g., at least substantially parallel to a principal movement direction of the particles). This is advantageous in that the expected inhomogeneities, in the form of particle strands along the principal movement directions of the particles in the flow, can be identified efficiently.

In a further embodiment, provision is made for determining the position to contain a superposition of the reconstructed particle position functions. For example, a superposition of the reconstructed particle position functions form a two-dimensional or three-dimensional image in spatial coordinates. Advantageously, an automatic particle detection based on such images is easily derivable and extendable as desired. To this end, many methods of image processing and pattern recognition (both statistical and deterministic methods) are conceivable and expedient. Naturally, a manual, visual interpretation is also possible in a simple manner.

In a particularly advantageous embodiment, provision is made for the detection method to be applied to a particle flow (e.g., a multiplicity of particles which move in a flow). After the positions of particles in the particle flow are determined, provision is made for those positions of particles belonging together due to an assumed, predetermined statistically-dependent distribution to be extracted. The positions are mapped onto a probability function. Advantageously, the employed deterministic signal model also allows conclusions to be drawn about the behavior of the present particle distribution in addition to the high adaptability to various situations. If the particle distribution follows a purely stochastic process, then the deviation from the specially defined, deterministic model is clearly identifiable in the result of the method. If a specific image in spatial coordinates arises within the scope of the method, detection of strand-shaped inhomogeneities in the flow is also efficiently performed based on the images via methods of image processing and pattern recognition.

Here, provision can be made for the probability function to be used to determine whether there is an inhomogeneous distribution of particles within the particle flow. If so, provision is made for the inhomogeneity to be localized based on at least one maximum of the probability function. For example, one possible maximum is the absolute maximum. This is advantageous in that localizing the inhomogeneity or the particle strand is automatable in a simple and efficient manner.

In accordance with a further embodiment, provision is made for reception signal and/or kernel (e.g., convolution kernels) to be each selected to have a complex value. The number of virtual positions of particles is advantageously reduced (e.g., the number of interferences induced by the convolution between the different functions when many particles are significantly reduced for image-based post-processing). That is, the virtual positions of particles are more readily manageable. A virtual position of a particle is understood here to mean a "false" particle position; the method suggests the existence of a particle even though none is situated there (e.g., a so-called "false positive").

In a further embodiment, provision is made for spectral tapering of the reception signal or kernel to be undertaken in each case. This is advantageous in that the waviness of the convolution result, caused by a band-restriction of the modulation, is reduced. The number of virtual particle positions or virtual points or the possible particle positions occurring in spatial coordinates in a two-dimensional or three-dimensional image is reduced. The particle visibility significantly improves in such a representation in the movement direction of the particles.

Additionally, provision can be made here for high-pass filtering of reception signal and/or kernel after the tapering. This is advantageous in that a resolution capability in a direction perpendicular to the movement direction of the particles is improved.

Some embodiments include a detection device for localizing at least one particle moving in the flow. The detection device includes a sensor for emitting a transmission signal and for detecting a reception signal. The detection device also includes an evaluation unit. A frequency and a phase of the reception signal are detectable by the evaluation unit, and, in the evaluation unit, the reception signal is convolvable with at least one kernel representing a conjugated, estimated channel pulse response. A reconstructed particle position function is formed, and a position of the particle is determinable from the reconstructed particle position function. For example, a microwave sensor may be used.

DESCRIPTION OF THE FIGURES

Further features of the invention emerge from the following description of preferred exemplary embodiments of the invention, and from the figures. Here.

In the Figures, the same or functionally equivalent elements are provided with the same reference signs.

DETAILED DESCRIPTION

Figure 1:
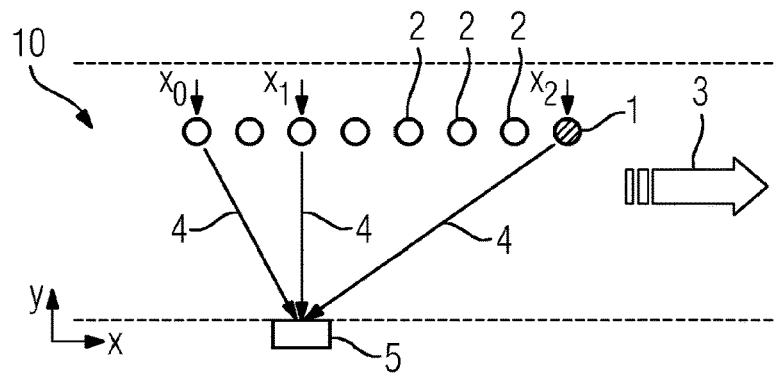
FIG. 1 illustrates an exemplary particle flow in accordance with an embodiment of detection for localizing a particle.

FIG. 1 illustrates an exemplary particle flow that may be applicable to disclosed embodiments of detection methods for localizing a particle. Here, a particle 1 moves past a sensor 5 in a flow channel 10 in a manner parallel to the principal flow direction 3. Flow direction 3 is symbolized by an arrow. The particle 1 successively assumes different positions 2, that are all distributed parallel to the principal flow direction 3. In addition to the current position x2 of the particle 1, two earlier positions x0 and x1 of the particle 1 are also marked separately. Thus, the position x0 was taken up by the particle 1 at a time before the position x1, that was, in turn, taken up prior to the current position x2. In all of the positions assumed by the particle 1, the latter reflects a reception signal 4 in the direction of the sensor 5. The radial component of the movement of the particle relative to the sensor 5 (e.g. a microwave sensor) generates a frequency shift in the reflected reception signal 4 due to the Doppler effect. With the advancing movement of the particle 1 along the principal flow direction 3, there is a change in the aspect angle relative to the sensor 5. Consequently, there is a change in the radial component of the velocity relative to the sensor 5, as well as in the resulting Doppler shift. While the particle 1 "flies by", the reflected reception signal 4 experiences a continuous frequency and phase modulation (as illustrated in FIG. 2) that is characteristic and unique for the traveled trajectory of the particle 1 (e.g., for all previously taken up positions 2 of the particle 1 and the current position thereof).

Figure 2:
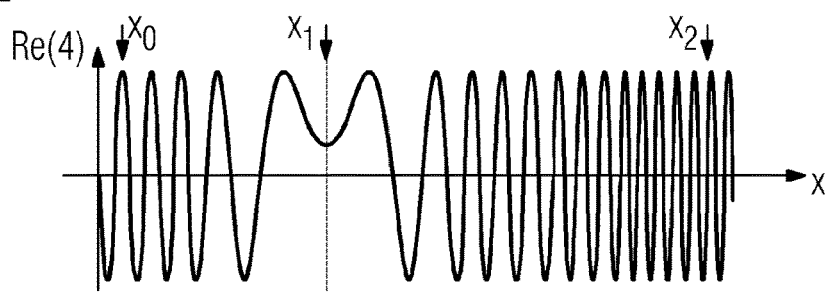
FIG. 2 illustrates an exemplary frequency and phase modulated reception signal corresponding to particle flow of FIG. 1.

FIG. 2 shows an exemplary frequency-modulated and phase-modulated reception signal 4 corresponding to the situation shown in FIG. 1. The real part of the reception signal 4 is plotted along the x-axis. FIG. 1 illustrates that the x-axis is oriented parallel to the principal flow direction 3. There is a different phase and frequency modulation in each case at the three positions x0, x1 and x2, corresponding to the positions x0, x1 and x2 of FIG. 1. Considered mathematically, the reception signal 4 therefore arises by convolving the channel pulse response or pulse response with a particle position function. The inverse problem is solved for reconstructing the position x0, x1, x2 etc. of the particle 1 by deconvolving with a conjugated, estimated pulse response represented by the kernel.

The underlying principle of Doppler modulation as a result of target movement, in conjunction with imaging methods may be found in the field of the naval and air forces under the term "inverse synthetic aperture radar". However, in those conventional methods, the target position is assumed to be known or explicitly measured; moreover, the dimensions of the considered objects have significantly larger sizes. The dimensions are more suitable for microwaves as a matter of principle, and different problems arise in that case.

Figure 3:
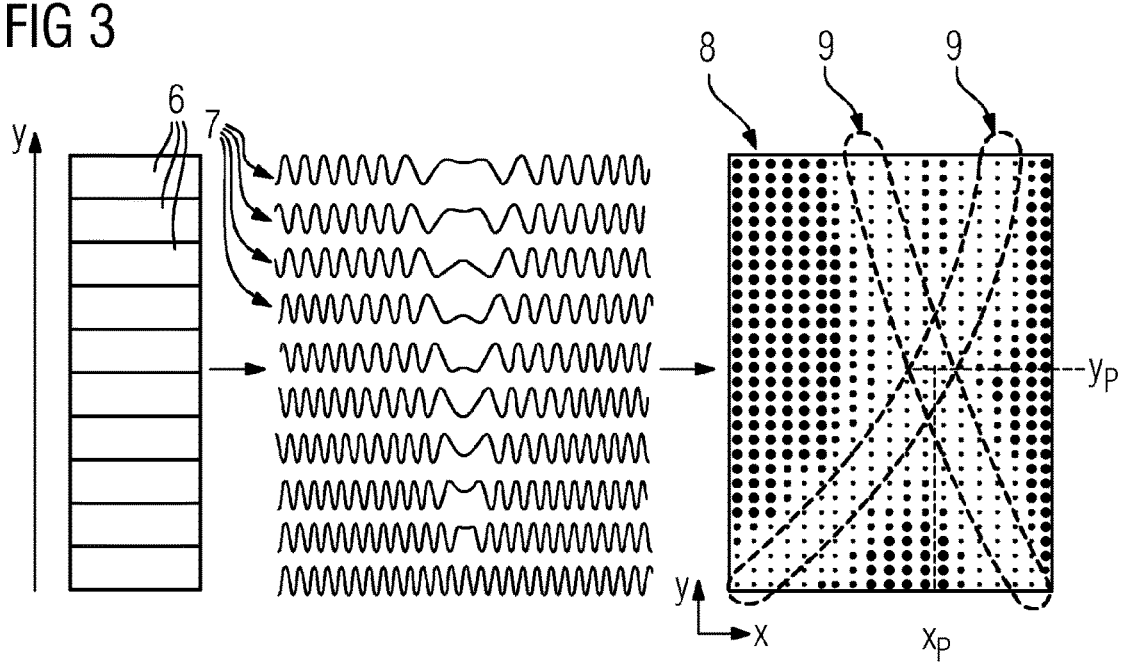
FIG. 3 illustrates a schematic of an exemplary embodiment with a plurality of used kernels.

FIG. 3 depicts a schematic of an exemplary embodiment using multiple kernels. A signal-adapted filter bank is based on a family of kernel functions (e.g., kernels 7) that correspond to a subset of the expected particle trajectories (e.g., the expected particle position functions and the corresponding phase-modulated reception signal 4). The flow channel 10 is initially subdivided into a plurality of sections 6 that all have an equal extent in the y-direction, i.e. perpendicular to the principal flow direction 3. At the same time, each section 6 respectively covers the whole flow channel 10 in the x-direction, parallel to the principal flow direction 3. However, in principle, the sections 6 can be selected in any way. What is important is a correct assignment of the kernels 7, as illustrated in the center of FIG. 3. Each of the kernels 7 corresponds to the section 6 directly to the left thereof. The kernels 7 are each convolved with the one reception signal 4 to form a particle position function. The individual results of the convolution are put together to form a two-dimensional image 8. The results are sorted in accordance with the arrangement of the sections 6 or of the kernels 7, as result of which a spatially accurate image of the particle position functions emerges. Large magnitudes of the reconstructed particle position function are depicted to be bright, and small magnitudes are depicted to be dark. Two lines 9 emerge, and the point of intersection determines the position of the particle. The position is made visible by way of the coordinates xP and yP. Thus, different convolution kernels (e.g., kernels 7) are formed within the flow. All convolution results are assigned to corresponding source positions and superposed with one another such that an two-dimensional image arises in spatial coordinates. An individual particle in this image may generate a x-shaped convolution result. What is decisive in this case for the obtained resolution is the modulation width and the exact reproduction of the modulation function in the kernel 7. Here, the maximum of a convolution result represents the position of the particle in the x-direction (e.g., in the direction of the principal flow direction 3). The selected modulation function in the kernel 7 determines the direction in the y-direction (e.g., perpendicular to the principal flow direction 3). A deviation of the phase center of the actual pulse response from the estimated pulse response is expressed in an offset of the result in the x-direction. A deviation of the modulation function of the actual pulse response from the estimated pulse response is expressed here in an offset of the result (e.g., the particle position function) in the y-direction.

Figure 4:
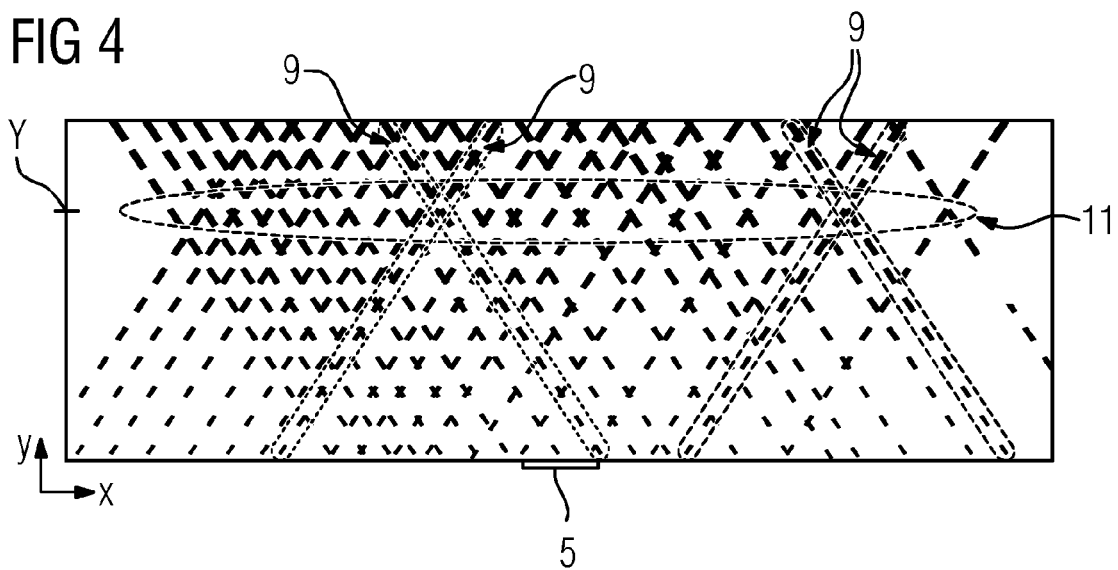
FIG. 4 illustrates a simulation result for a particle flow with an inhomogeneity that can be localized with one embodiment of detection for localizing a particle.

FIG. 4 depicts a simulation result for a particle flow having an inhomogeneity that can be localized using one embodiment of the detection method. A multiplicity of crossing lines 9 are plotted along the spatial coordinates in the x and y direction. To aid orientation, the location of the sensor 5 has also been plotted. The particle flow, the particles 1 that have been detected and depicted graphically, flows past the sensor 5 in a manner parallel to the x-direction. A homogeneous particle distribution in the flow follows a stochastic process. However, in the case of an inhomogeneity (e.g., a strand formation, a statistical dependence of the particles 1 that form the strands) arises in the y-direction. In accordance with the relationship illustrated in FIG. 3, the modulation signal of such a strand consists of the superposition of all frequency and phase contributions of the individual particles 1. In the case of a strand 11, a succession of points of intersection of lines 9 emerges in the reconstructed image. When many particles 1 are present, many crossing line pairs that do not have physical particles as a cause arise. The crossing line pairs not associated with physical particles are also referred to as virtual points of intersection or virtual particles. The virtual particles may be identified and eliminated via suitable pre- and post-processing steps. It is expedient to select reception signals 4 and the kernel 7 to have complex values since the convolution requires the conjugate of the pulse response. Although particles 1 are detectable with real-valued basis signals, the number of virtual particles or the set of "convolution interference" in the case of many particles 1 is significantly more difficult to manage for image-based post-processing. It is also expedient to undertake spectral tapering of reception signal 4 and kernel 7 for reducing the waviness of the convolution result that is caused by the band-restriction of the modulation. This significantly reduces the number of virtual particles and significantly improves the particle visibility in such a representation in the transverse direction, e.g., in the x-direction. Finally, high-pass filtering of reception signal 4 and kernel 7 may be performed to improve the resolution capability in the y-direction again, that was made worse by tapering. High-pass filtering may be performed in advance, shifting a weighting toward a steady component; high-pass filtering can also be performed without tapering in advance. Then, it is possible to identify a strand 11 along the position Y. Hence, if related to the flow channel 10 (e.g. a feed line to the burner in a coal power plant) it is possible to carry out strand-independent mass flow determinations, detect inhomogeneities in an air-coal dust mixture, and introduce countermeasures in order to return to homogeneous mixing.

Figure 5:
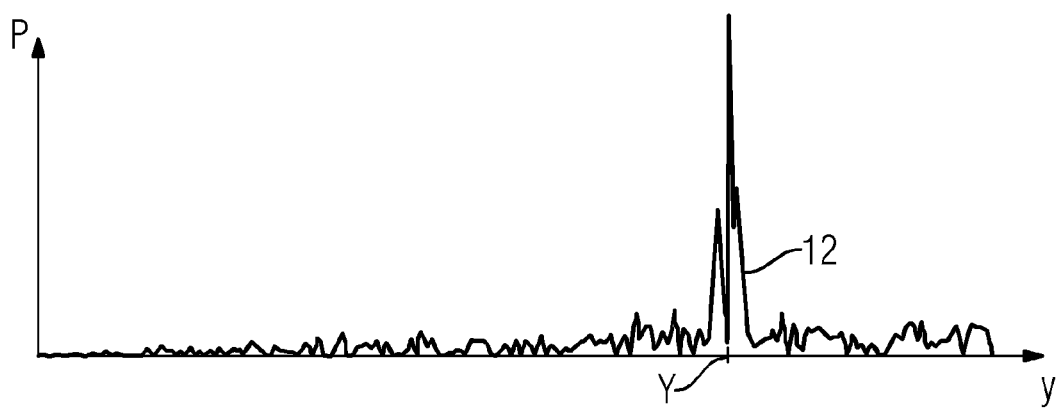
FIG. 5 illustrates a probability function extracted from the example in FIG. 4.

FIG. 5 depicts a probability function 12 extracted from the image of FIG. 4. Here, a relative probability P is plotted along the y-direction, the direction perpendicular to the principal flow direction 3. A maximum at the position Y, as illustrated in FIG. 4, is the position of the strand 11, can clearly be identified. Hence, the position Y of the strand 11 can also easily be identified automatically. Here, the probability function 12 was created via the points of intersection of the lines 9. The points of intersection that belong together are the group of points with an assumed statistically dependent distribution initially extracted via suitable image-processing methods and subsequently mapped onto a probability function 12. These probabilities then serve as a decision basis for a detection of the strand 11. Since extraction of the points of intersection is based on spatial coordinates, the distance of the strand 11, or of the particles 1 contained in this strand 11, is known directly. By way of example, if the strand 11 should now be localized in a three-dimensional space, it is possible to uniquely determine the position of the strand 11 in the three-dimensional space via further sensors that are arranged distributed in space with the disclosed detection methods and, for example, by triangulating the distances.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A detection method for localizing at least one particle moving in a flow, the detection method comprising:
   emitting a transmission signal by a transmitter of a detection device;
   receiving a reflected reception signal, wherein the reflected reception signal is frequency-modulated and phase-modulated in comparison with the transmission signal, by a receiver of the detection device;
   convolving, by an evaluation unit of the detection device, the reflected reception signal with at least one kernel, wherein the at least one kernel is representative of a conjugate estimated channel pulse response, to form a reconstructed particle position function; and
   determining, by the evaluation unit of the detection device, a position of the particle from the reconstructed particle position function.

2. The detection method of claim 1, wherein the convolution is carried out multiple times, each with a different kernel of a plurality of kernels, wherein each kernel of the plurality of kernels corresponds to a different expected particle position function, and wherein particle position is determined from the plurality of reconstructed particle position functions.

3. The detection method of claim 2, wherein each kernel of the at least one kernel is assigned to particle position functions of the particle, wherein the particle position functions are distributed along a principal movement direction of the flow.

4. The detection method of claim 3, wherein determining the position further comprises:
   superpositioning the plurality of reconstructed particle position functions into a two-dimensional or three-dimensional image in spatial coordinates.

5. The detection method of claim 3, wherein the detection method is applied to a plurality of particles in the particle flow, the method further comprising:
   extracting associated positions of the plurality of particles based on an assumed predetermined statistically-dependent distribution; and
   mapping the extracted associated positions of the plurality of particles onto a probability function.

6. The detection method of claim 3, further comprising:
   selecting the reflected reception signal, the at least one kernel, or the reflected reception signal and the at least one kernel to have a complex value.

7. The detection method of claim 3, further comprising:
   spectrally tapering the reflected reception signal, the at least one kernel, or the reflected reception signal and the at least one kernel.

8. The detection method of claim 2, wherein determining the position further comprises:
   superpositioning the plurality of reconstructed particle position functions into a two-dimensional or three-dimensional image in spatial coordinates.

9. The detection method of claim 8, wherein the detection method is applied to a plurality of particles in the particle flow, the method further comprising:
   extracting associated positions of the plurality of the plurality of particles based on an assumed predetermined statistically-dependent distribution; and
   mapping the extracted associated positions of particles onto a probability function.

10. The detection method of claim 8, further comprising:
    selecting the reflected reception signal, the at least one kernel, or the reflected reception signal and the at least one kernel to have a complex value.

11. The detection method of claim 2, wherein the detection method is applied to a plurality of particles in the particle flow, the method further comprising:
    extracting associated positions of the plurality of particles based on an assumed predetermined statistically-dependent distribution; and
    mapping the extracted associated positions of the plurality of particles onto a probability function.

12. The detection method of claim 2, further comprising:
    selecting the reflected reception signal, the at least one kernel, or the reflected reception signal and the at least one kernel to have a complex value.

13. The detection method of claim 2, further comprising:
    spectrally tapering the reflected reception signal, the at least one kernel, or the reflected reception signal and the at least one kernel.

14. The detection method of claim 1, wherein the detection method is applied to a plurality of particles in the particle flow, the method further comprising:
    extracting associated positions of the plurality of particles based on an assumed predetermined statistically-dependent distribution; and
    mapping the extracted associated positions of the plurality of particles onto a probability function.

15. The detection method of claim 14, further comprising:
    determining whether the particle flow includes an inhomogeneous distribution of particles based on the probability function; and
    localizing the inhomogeneity based on at least one maximum of the probability function, wherein the at least one maximum includes an absolute maximum.

16. The detection method of claim 15, further comprising:
    selecting the reflected reception signal, the at least one kernel, or the reflected reception signal and the at least one kernel to have a complex value.

17. The detection method of claim 14, further comprising:
    selecting the reflected reception signal, the at least one kernel, or the reflected reception signal and the at least one kernel to have a complex value.

18. The detection method of claim 1, further comprising:
    spectrally tapering the reflected reception signal, the at least one kernel, or the reflected reception signal and the at least one kernel.

19. The detection method of claim 18, further comprising:
    high-pass filtering the reflected reception signal, the at least one kernel, or the reflected reception signal and the at least one kernel.

20. The detection method of claim 1, further comprising:
selecting the reflected reception signal, the at least one kernel, or the reflected reception signal and the at least one kernel to have a complex value.

* * * * *